United States Patent [19]

Kawauchi et al.

[11] Patent Number: 5,121,438

[45] Date of Patent: Jun. 9, 1992

[54] APPARATUS FOR INSPECTING ARTICLES

[75] Inventors: Yasunobu Kawauchi, Fussa; Yasuo Ogino, Nagaizumi; Shozo Ogata, Kannami, all of Japan

[73] Assignee: Toshiba Kikai Kabushiki Kaisha, Tokyo, Japan

[21] Appl. No.: 442,020

[22] Filed: Nov. 28, 1989

[30] Foreign Application Priority Data

Nov. 30, 1988 [JP] Japan .................. 63-303218

[51] Int. Cl.$^5$ .............................................. G06K 9/00
[52] U.S. Cl. ....................................... 382/8; 358/106; 356/237
[58] Field of Search ............................ 382/8; 358/107; 356/237

[56] References Cited

U.S. PATENT DOCUMENTS 4,555,799 11/1985 Kodama et al. ................. 382/8
4,727,419 2/1988 Yamada et al. ................. 382/8

Primary Examiner—Leo H. Boudreau
Assistant Examiner—David Fox
Attorney, Agent, or Firm—Koda and Androlia

[57] ABSTRACT

In apparatus for successively inspecting an article, for example a telephone cable connector having a plurality of two dimensionally arranged connecting pins, the article is successively conveyed to and mounted on an inspecting table, an image pick-up camera is stepwisely moved for photographing all portions of the connector, and the direction of movement of the camera is alternately reversed.

3 Claims, 5 Drawing Sheets

APPARATUS FOR INSPECTING ARTICLES

BACKGROUND OF THE INVENTION

This invention relates to apparatus for inspecting an article, for example an electric connector having a plurality of connecting pins such as a telephone cable.

Heretobefore, the inspection of the material or the type of plating of the connecting pins of a telephone cable connector has been made by observation with eyes of a workman.

In recent years inspection apparatus has been proposed wherein a connector to be inspected is positioned on a table and a camera is moved from one end to the other end of the connector for photographing successive regions (frames) of the connector, thereby automatically identifying picture images.

FIG. 4 is a block diagram showing one example of such inspecting apparatus. An already proposed apparatus shown in FIG. 4 comprises a cable connector 10 to be inspected mounted on an inspecting table 20 which is controlled by an inspection table controller 21, an image pick-up member 40 which photographs the connecting pins of the connector 10 for outputting picture image signals as analog signals, a picture image processing member 50 for converting analog signals into multivalue digital signals and then storing the digital signals, an identifying processing member 60 which compares histograms of multivalue digital signals supplied from the picture image processing member 50 and then effects identification based on the result of comparison, a computer system 30 effecting an overall control of various members, and cables 31 for interconnecting various members.

The image pick-up member 40 comprises a light source 41 for illuminating the connecting pins of the connector 10, an image pick-up elements 43 for photographing pin heads and nearby portions and a condenser lens 42 for focussing picked-up images on an image pick-up elements. The picture image processing member 50 comprises an analog-digital (A/D) converter 51, a multivalue digital signal memory means 52 for temporarily storing the multivalue digital signals, a histogram processor 53 for converting multivalue digital signals into signals of the histogram form, and memory means 54 for temporarily storing the data of the histogram. The identifying and processing member 60 comprises a characteristic extracting and computing unit 61 for extracting characteristics or features from the histogram data, a reference characteristic pattern file 63 for storing characteristic data of a standard connector, a pin arrangement information file 64 and a comparator 62 comparing characteristic pattern data of the connector 10 with the reference characteristic pattern data, not shown.

The information from the image pick-up element 43 is transmitted to the comparator 62 successively through A/D converter 51, multivalue digital signal memory means 52, histogram processor 53, temporary memory means 54, and characteristic extracting and computing unit 61. The informations from pin arrangement information file 64 are applied to reference characteristic pattern data file 63 and the information outputted from the reference characteristic pattern data file 63 in response to the informations from the pin arrangement information file 64 are applied to the reference characteristic pattern data file 63, and informations outputted from the reference characteristic pattern data file 63 in response to the informations supplied thereto are inputted to comparator 62 whereby the comparator 62 outputs the result of inspection.

The picture image processing member 50, identifying and processing member 60, inspection table controller 21 and computer system 30 exchange therebetween such informations as the control signals. The control signal is supplied to image pick-up member 43 from computer system 30, while a control signal is supplied to the inspection table 20 from inspection table controller 21.

FIG. 5 is a flow chart showing program steps or procedures of a prior art inspecting apparatus.

At first the inspection table is positioned at a predetermined position. The connecting pins of the first row and the first column are set in a predetermined region by making i=1 and j=1. Then at step S11, the pins are photographed by pick-up elements 43. The picture image informations thus picked-up are decomposed into mxn picture elements which are temporarily stored as analog signals, where m and n represent positive integers, respectively. The analog signals are sent to A/D converter 51 via a signal processing unit, not shown, which amplifies and removes noise from the analog signals. A/D converter 51 converts inputted analog signals into multivalue digital signals by adding informations of several bits representing the tone of white and black to respective picture elements of mxn. The multivalue digital signals are temporarily stored in multivalue digital signal memory means 52 at step S12. Then the multivalue digital signals stored in memory means 52 are converted into histogram data representing picture elements respectively corresponding to 64 tones by histogram processor 53 and the histogram data thus converted are temporarily stored in memory means 53 at step S13.

At step S14, the characteristic extracting and computing unit 61 extracts characteristic pattern data for respective pins from the histogram data stored in the memory means for sending extracted characteristic pattern data to comparator 62.

In the identifying and processing member 60, pin arrangement informations for respective connector models are represented in binary forms in the order of $$\sum_{i=1}^{n}, \sum_{j=1}^{2} ij$$

and the pin arrangement informations are stored in pin arrangement information file 64. Symbols A (110010...) and other symbols represent the pin arrangement informations.

As shown in FIG. 4, the computer system 30 effecting an overall control of a series of processing means is connected to various members by cables 31 for transmitting informations relating to a connector model to be inspected and connecting pins thereof to the identifying and processing member 60. In synchronism with the inputting of characteristic pattern data of the pins to be inspected to comparator 62, type informations of pins corresponding to the pins to be inspected are read out from the pin arrangement information file 64 and sent to the reference characteristic pattern data file 63. The reference characteristic pattern data file 63 supplied with the connector model information and the pin type informations reads out a corresponding reference characteristic pattern data and sends the read out data to comparator 62 which compares the characteristic pattern data of the pins to be inspected with the characteristic pattern data at step S15. As a result of comparison, the comparator 62 outputs a signal. When both data coincides with each other the program is advanced to the inspection of a next pin. Like the pin arrangement information, the inspection of the pins is performed in the order of (1,1) (1,2), (2,1) . . . (n,2) (surpentine form). Upon completion of the inspection of pins in a predetermined region the image pick-up member is advanced one step for inspecting pins in a next region (step and repeat operation). By repeating this operation all pins in one region is inspected at step S16. When a reject pin is detected at the end point or at an intermediate point, at step S17, the comparator 62 outputs a signal showing a noncoincidence. In response to this signal satisfactory connectors and rejects are classified at steps 16 and 17.

With the inspecting apparatus thus far described where the pins in all regions of a connector have been inspected or when a reject pin is detected in the course of inspection, the inspected connector is taken out and a next connector is mounted on a predetermined position. Concurrently therewith, it has been necessary to return the image pick-up camera to the inspection starting position.

FIG. 6 is a time chart of a case wherein a single connector is divided into n frames (see FIG. 3). As shown, when the picture image of the (n−1)th frame is picked-up and stored in the memory means 52, the picture image identifying processing of that frame and step by step movement of the pick-up camera to the (n)th frame are started simultaneously. At this time, when the time $T_1$ required for positioning the camera is shorter than the time $T_3$ required for identifying and processing the picture image of the (n−1)th frame, there is no fear of causing a useless waiting time for the identification and inspection so that the identifying and processing time of one frame becomes equal to $(T_2+T_3)$.

Generally, the time required for picking-up a picture image with a camera is nearly equal to that of a television pick-up camera. In other words, since the time required for picking-up one frame is 1/30 sec, $T_2=33.3$ ms, or $2T_2$ in the longest time. Now assume that the pin diameter of a connector to be inspected is about 0.3 mm, that the pitch of the pins is 2.5 mm, and that the pins are arranged in two rows, a frame of a size of about 10 mm × 19 mm can be processed where a picture image of one frame is divided into 256×256. As a consequence, it become possible to identify eight pins by a single picture image pick-up operation. The identifying and processing time $(T_2 \cdot T_3)$/number of pins in one frame necessary for each pin is desired to be less than 1000 ms to be commensurate with the tact time of a pin inserting machine used in the previous step. The apparatus described above can satisfy this requirement. In order to perform an operation not accompanying the waiting time described above, the average speed of the step by step feeding of the camera should be larger than frame length 10 mm/number of pins (8×0.15)=12.5 mm/sec. This can readily be realized by an ordinary positioning technique.

The connector of the nth frame which has been inspected is taken out from the inspecting apparatus and a new connector is mounted on the inspection table.

A connector of the nth frame whose inspection has been completed is taken out from the inspecting apparatus and a new connector is mounted on the inspection table. Such taking out and positioning of the connector can be accomplished in about 1 second wherein the connector has a length of 150 mm. This time represents the waiting time between successive taking out and positioning times. If it is possible to immediately start the inspection after positioning a new connector, successive steps of instruction can be performed smoothly. This condition can be satisfied by returning the camera to the inspection position of the first frame of the next connector in a relation of $T_n \leq T_3 + T_L$ after picking-up the picture image of the nth frame, where $T_L$ represents a time necessary for mounting a connector onto the inspection table and then positioning, that is 1 second described above. In a typical connector wherein the pin pitch is 2.5 mm, and the number of pins is 32×2 rows, the time $T_3+T_L=8\times0.1+1=1.8$ sec. so that an average return speed of the camera should be $(64/8-1)\times8/2\times2.5/1.8=38.9$ mm/sec. so that during a running not related to the inspection, a camera supporting member is required to run at a speed 3 times of the speed at the time of inspection.

As a consequence, although the inspecting apparatus described above can eliminate most of the defects of previous apparatus there are many problems in the drive and control of the camera regarding economy, stability of the machine and reliability.

SUMMARY OF THE INVENTION

It is an object of this invention to provide a novel inspecting apparatus for inspecting articles, for example a telephone cable connector, which can save man power, and can improve the economy, inspection efficiency, and reliability of the inspection.

According to this invention there is provided apparatus for inspecting articles comprising an inspecting table; means for successively conveying the articles onto the inspecting table and for positioning each article at a predetermined position of an upper surface of the inspecting table; image pick-up means for photographing the article, portions thereof to be photographed being divided into a plurality of continuous frames; means adapted to support the image pick-up means for stepwisely moving the image pick-up means in a unit of the frame for photographing all of the portions; drive means for alternately reversing the direction of movement of the image pick-up means, means responsive to the direction of movement for successively converting picture image signals outputted from the image pick-up means into digital informations in the frame units; and picture image identifying means for extracting characterizing pattern data from the digital informations for identifying the articles.

DESCRIPTION OF THE PREFERRED EMBODIMENT

Figure 1:
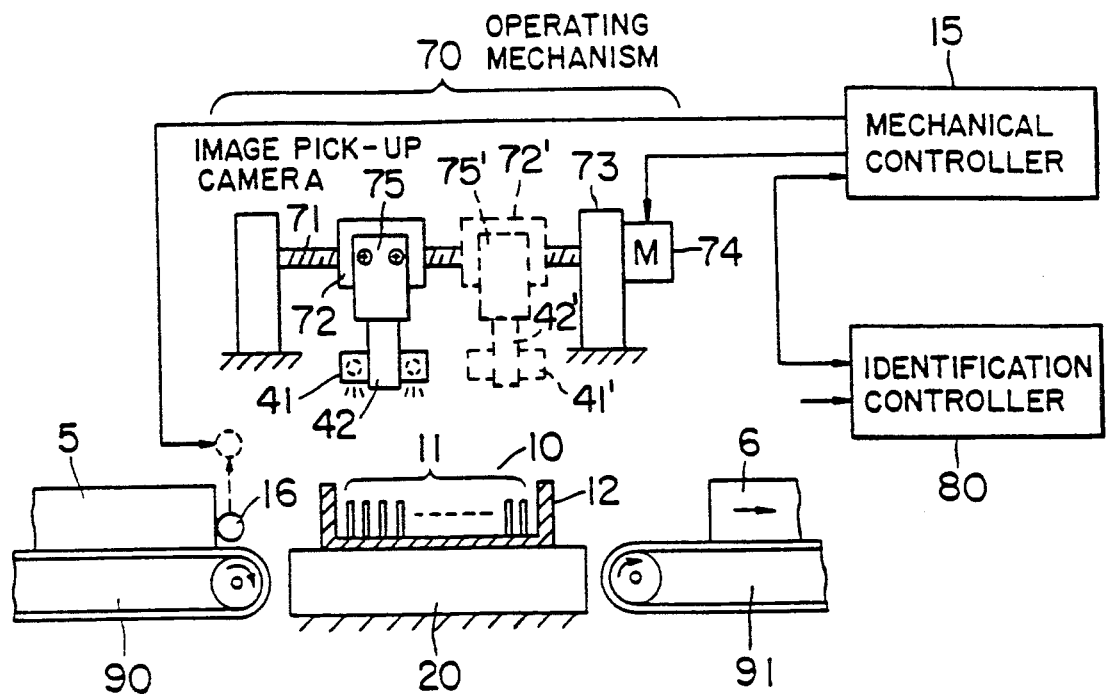
FIG. 1 is a diagrammatic representation partly in blocks showing a preferred embodiment of the inspecting apparatus according to this invention.
Figure 4:
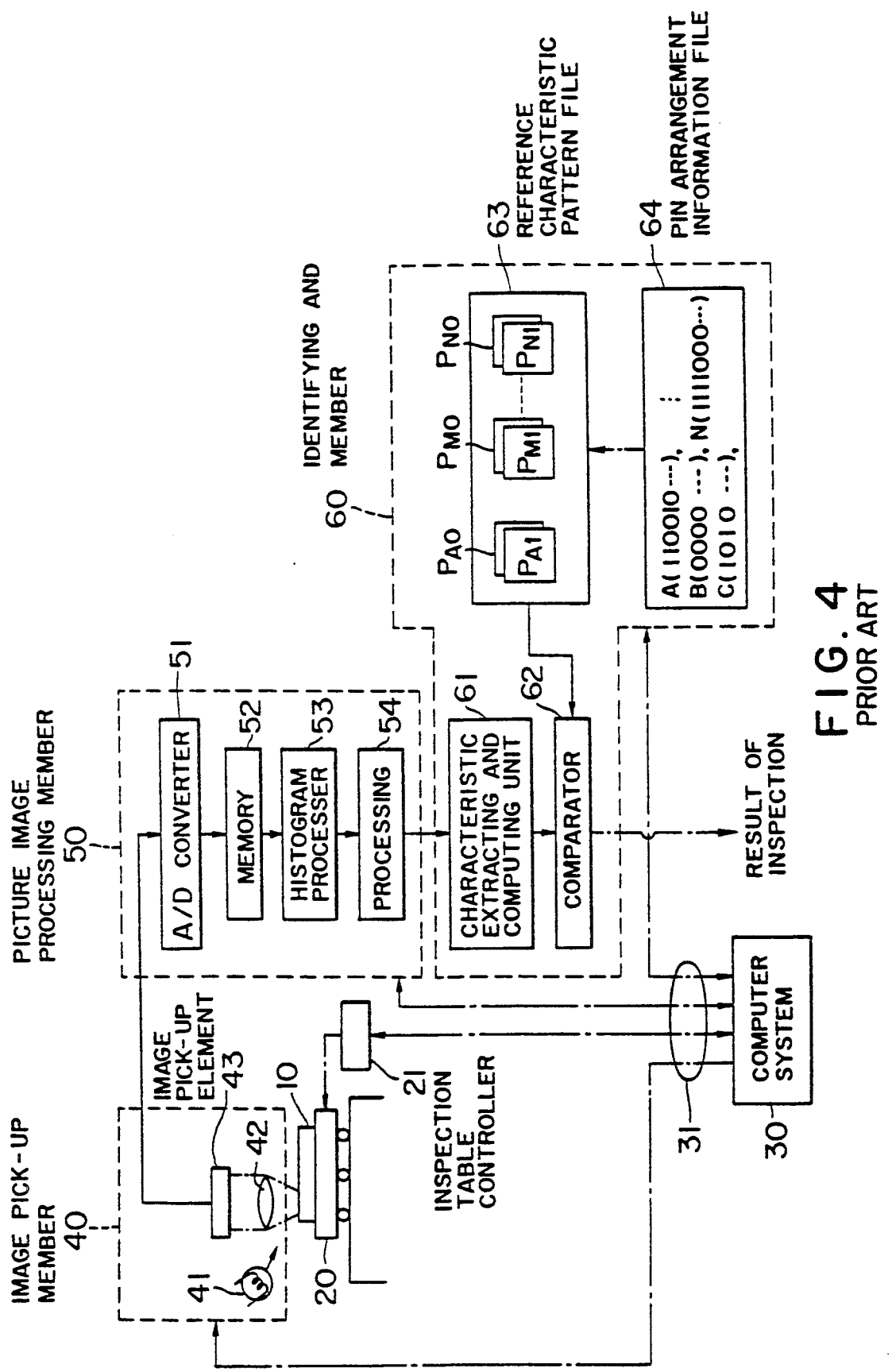
FIG. 4 is a connection diagram showing inspecting apparatus which has been proposed previously.
Figure 5:
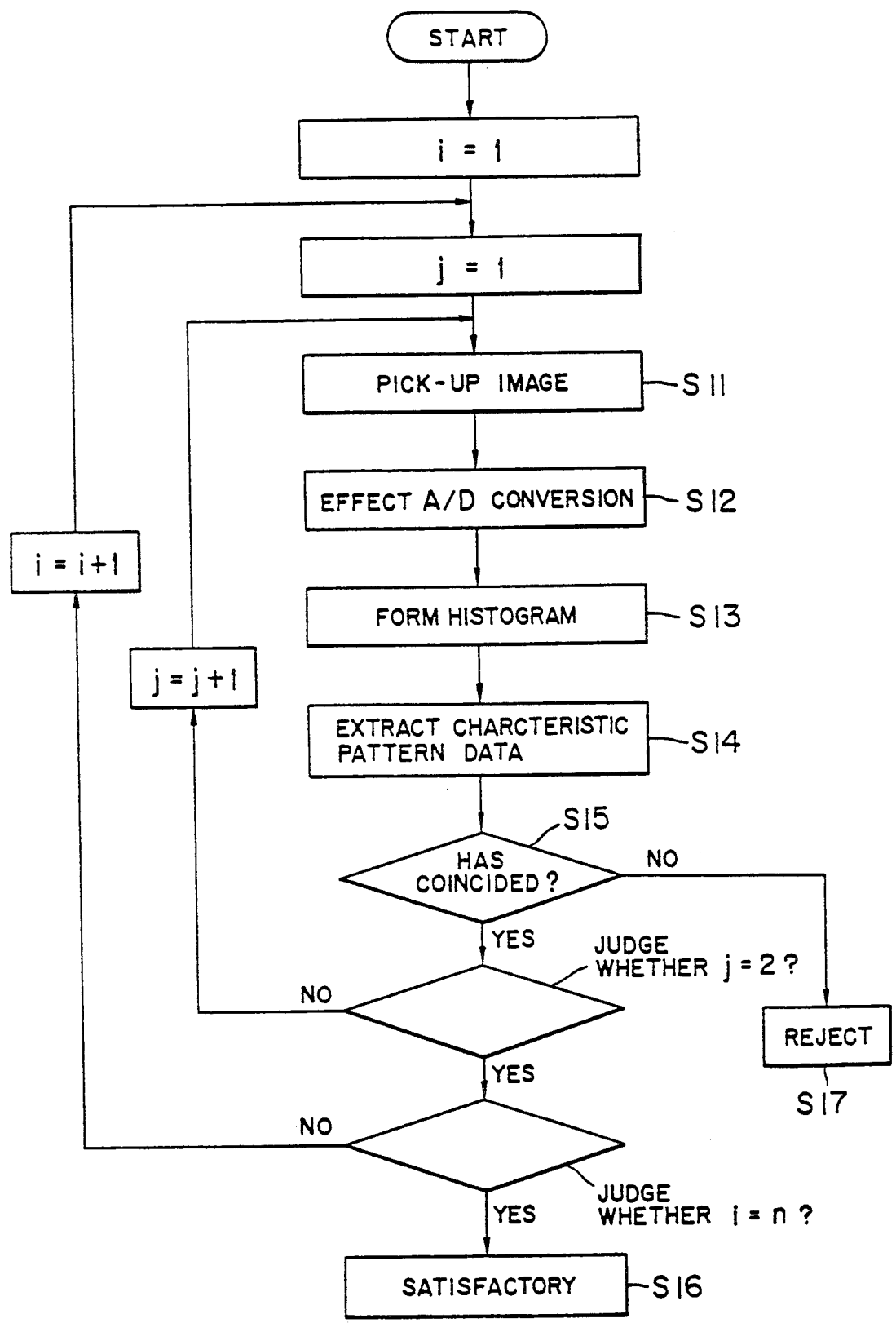
FIG. 5 is a flow chart showing the program steps of the inspection apparatus shown in FIG. 4.
Figure 6:
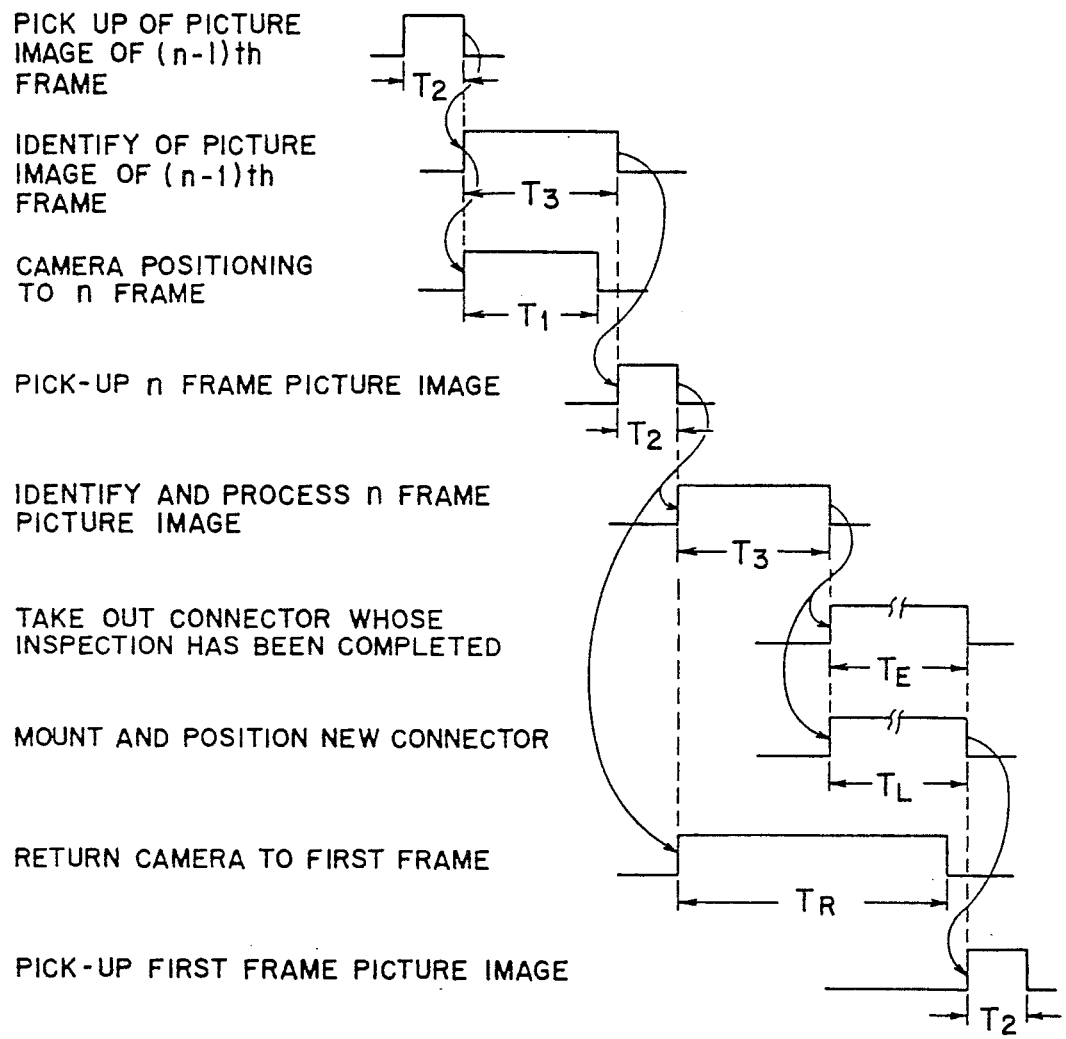
FIG. 6 is a time chart showing a case wherein the connector is divided into n frames.

In the following description, connecting pins of a telephone cable connector are shown as articles to be inspected, which are arranged two dimensionally. In FIG. 1, elements different from those shown in FIG. 4 will be described in detail.

In FIG. 1, an operating mechanism 70 is made up of an image pick-up camera 75, a ball screw 71, a nut 72 mating the ball screw, supporting members 73 rotatably supporting ball screw 71, an electric motor M for rotating ball screw 71, and a mechanical controller 15. A lens 42 and a light source 41 are mounted on the image pick-up camera 75. On an inspecting table 20 is mounted a cable connector including pins 11 to be inspected and a housing 12. On the opposite sides of table 20 are disposed a conveyor 90 for conveying to the table 20 a connector 5 to be inspected next, and a conveyor 91 for conveying a cable connector whose inspection has been completed, both conveyors being run continuously.

Upon completion of the inspection of a cable connector 10 mounted on the table 20, an identification controller 80 sends a completion signal to a gate circuit 16 via mechanical controller 15 so as to remove inspected connector 10 from table 20 and to feed and position a connector 5 to be inspected next on the table 20.

Figure 3:
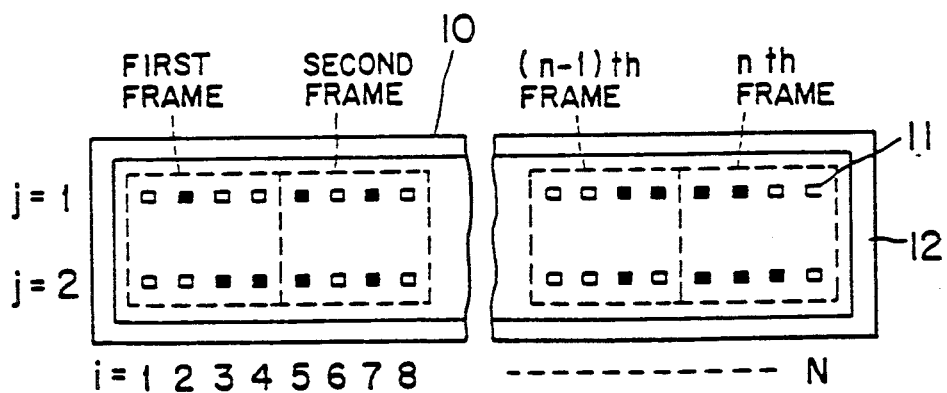
FIG. 3 is an end view of a cable connector wherein the connector is divided into n frames.

Identification and inspection of the connection pins are performed such that the size of the frame 12 is selected as shown in FIG. 3 in accordance with a resolution required for the identification of a picture image and the pins are inspected for each unit frame. The method of identification is the same as a prior art method.

Figure 2:
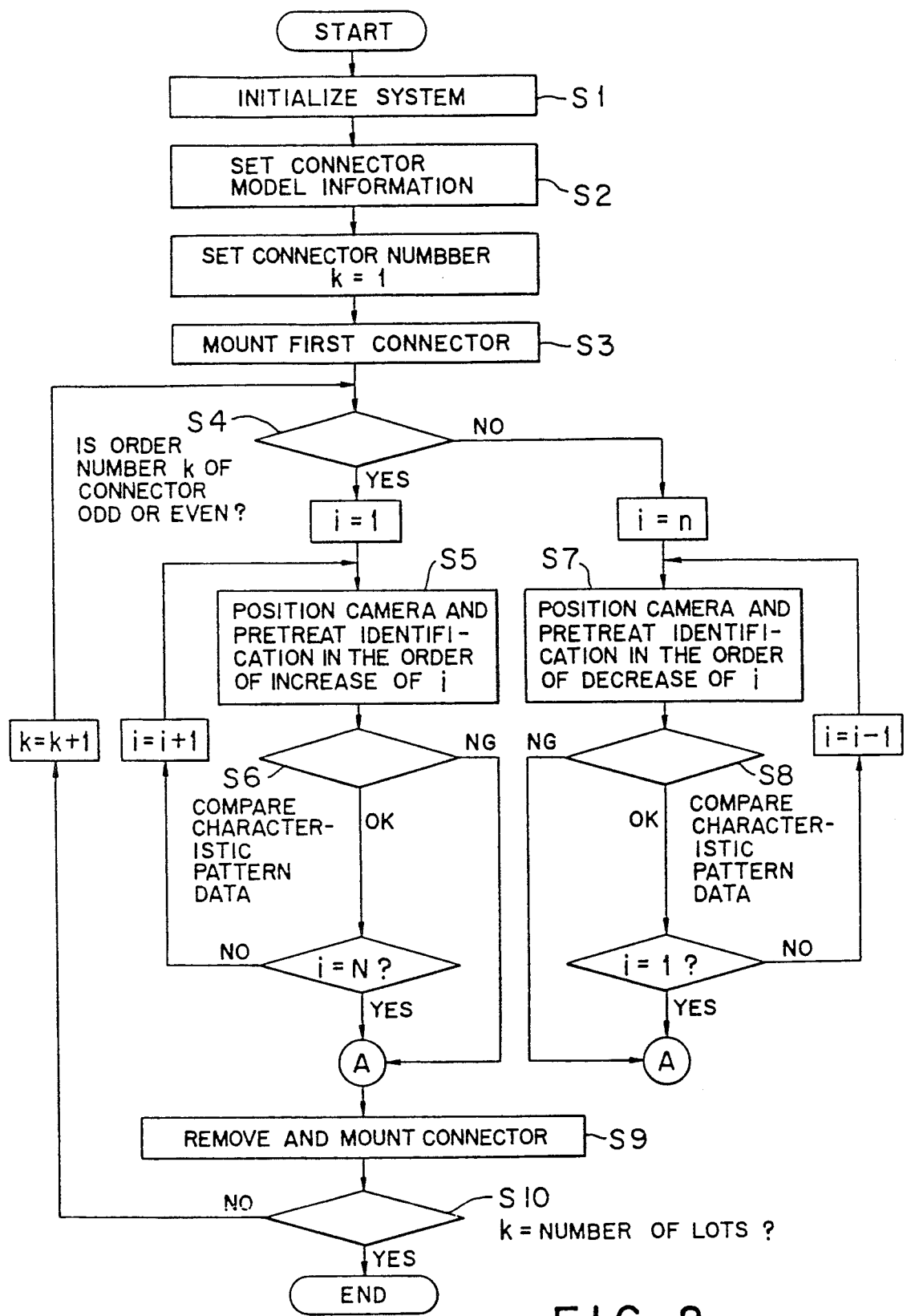
FIG. 2 is a flow chart showing program steps of the inspecting apparatus shown in FIG. 1.

Before starting inspection of a lot unit, at step S1 shown in FIG. 2, the system is initialized. Then at step S2, a connector model number of that lot, the lot size and other data necessary for the inspection are transmitted from a host computer. It should be understood that the pin arrangement information and a characteristic pattern data used as a reference of identification are stored in a file.

When a series of preparation steps described above are completed, at step S3 a first connector to be inspected of that lot is mounted on the table 20.

At step S4, a judgment is made as to whether the order number of the connector to be inspected is even numbered or odd numbered. Where the order number is odd, at step S5, the camera is positioned (step and repeat operation) and pretreatment of identification is effected from pick up of a frame picture image and extraction of a characteristic pattern data, starting from a pin row i=1 of the first frame, and in synchronism with this step, at step S6 characteristic pattern data comparison and identification processings are executed up to i=N. Where the order number k of a connector to be inspected is an even number, at step S7 the camera positioning and the identification pretreatment are executed in accordance with the decreasing order from i=N. In synchronism therewith, at step S8 the characteristic comparison and identification treatments are executed until i=1.

Irrespective of the odd or even of the order numbers, when inspections of the whole frames have been completed or where a reject pin is detected during inspection, the inspected connector is transferred onto conveyor 91 and a connector to be inspected next is mounted onto table 20.

Finally, at step S10, a judgment is made as to whether the order number k of a connector to be inspected becomes equal to the number of lots. Where the result of judgment executed at step S10 is NO, the program is returned to step S4 for executing again step S4 and succeeding steps, whereas when the result of judgment is YES the program is terminated.

Although many types of the description of the arrangement information may be used for each connector model in the same manner as in the prior art, where pin positions of the connector shown in FIG. 3 are denoted by Kij and where the pin types are selected as two, that is 1 and 0, it is possible to express $$\sum_{i=1}^{N} (k_1, j = 1, k_1, j = 2) = (1,1), (0,1), (1,0), (1,0) \ldots$$

for the first frame and $$(0,0), (0,0), (1,0), (1,0) \qquad (1)$$

for the nth frame. As a consequence, in this case, where k of the connector number is an odd number the inspections are performed from (1,1) of the first frame to (1,1) of the nth frame in the order of increasing i, whereas where k is an even number, the inspections are performed from (1,1) of the nth frame to (1,1) of the first frame in the order of decreasing i. For inspections of both directions, the step like feeding of the camera is performed, according to frame units.

As above described, by reversing the direction of movement of the camera it becomes possible to perform the inspection without accompanying the trouble of waiting time.

Although in the foregoing embodiment a single camera was used it is possible to use two cameras. Such a two camera embodiment is indicated by the elements down in dashed lines, in FIG. 1 and comprise light source 41', lens 42', nut 72' and second image pick-up camera 75'. In this case the cameras are controlled and mounted on a moving member having such differential mechanism that when one of the cameras reaches the image pick-up region of the first frame of a connector, the other camera would be positioned at the other end.

It should also be understood that an article to be inspected is not limited to the connector of a telephone cable. For example connectors for use in a bus line of a computer having a number of connecting pins can also be inspected.

As above described, with the inspecting apparatus embodying the invention the direction of inspection is reversed for successive articles to be inspected so that it is possible to improve the stability, reliability and economy of the inspection.

We claim:

1. Apparatus for inspecting articles which are arranged two-dimensionally, comprising:
   an inspecting table;
   means for successively conveying said articles onto said inspecting table and for positioning each article at a predetermined position of an upper surface of said inspecting table;
   image pick-up means for photographing said article, portions thereof to be photographed being divided into a plurality of continuous frames each having a characteristic pattern;

means adapted to support said image pick-up means for stepwisely moving said image pick-up means in a unit of said frame for photographing all of said portions in a certain specific direction and a direction opposite said certain direction;

drive means for alternately reversing direction of movement of said image pick-up means between said certain specific direction and said direction opposite said certain specific direction;

storage means for storing said characteristic pattern of each frame of a standard article, as reference pattern data;

means responsive to said direction of movement for successively converting picture image signals outputted from said image pick-up means into digital information in said frame units; and picture image identifying means for extracting characteristic pattern data from said digital information for identifying said articles, and for identifying a pattern by comparing extracted characteristic pattern data of one frame with said reference pattern data of corresponding frame stored in said storage means in accordance with whether said image pick-up means moves in said certain specific direction or said direction opposite said certain specific direction.

2. The apparatus according to claim 1 wherein said means adapted to support said image pick-up means supports a pair of image pick-up means such that when one of said image pick-up means reaches a front end of said article, the other image pick-up means is positioned at a rear end of said article on said inspecting table.

3. The apparatus according to claim 1 wherein said article is a connector of a telephone cable and provided with a plurality of connecting pins.

* * * * *